United States Patent [19]

Urdal et al.

[11] Patent Number: 5,128,450

[45] Date of Patent: Jul. 7, 1992

[54] NONGLYCOSYLATED HUMAN INTERLEUKIN-3 ANALOG PROTEINS

[76] Inventors: David L. Urdal, 6826 55th Ave. NE., Seattle, Wash. 98115; Helmut M. Sassenfeld, 4098 Mattson Pl., NE., Bainbridge Island, Wash. 98110

[21] Appl. No.: 374,667

[22] Filed: Jun. 30, 1989

[51] Int. Cl.$^5$ .................. C07K 13/00; A61K 37/02
[52] U.S. Cl. ........................ 530/351; 530/824; 424/85.2; 424/85.1; 435/69.52; 930/141; 935/49; 935/50
[58] Field of Search ............. 530/351; 424/85.2, 85.1; 435/69.52; 930/141

[56] References Cited

U.S. PATENT DOCUMENTS 4,877,729 10/1989 Clark et al. ........................ 435/68

FOREIGN PATENT DOCUMENTS 0138133 9/1984 European Pat. Off. .
WO8804691 6/1988 World Int. Prop. O. .
WO8806161 8/1988 World Int. Prop. O. .

OTHER PUBLICATIONS

Clark-Lewis, Science 231, 1986, pp. 134–138.
Dunbar et al., Science, 1989, p. 1493.
Growth Factors and their Receptors; Genetic Control and Rational Application, Alan R. Liss, 1989, pp. 229–238.
Ihle et al., "Regulation of T Cell Differentiation: in vitro induction of 20a-Hydroxysteroid Dehydrogenase in Splenic Lymphocyte from Athymic Mice by a Unique Lymphokine," J. Immunol. 126:2184 (1981).
Fung et al., "Molecular Cloning of cDNA for Murine Interleukin-3," Nature 307:233 (1984).
Yokota et al., "Isolation and Characterization of a Mouse cDNA Clone that Expresses Mast-Cell Growth-Factor Activity in Monkey Cells," Proc. Natl. Acad. Sci. 81:1070 (1984).
Yang et al., "Human IL-3 (multi-CSF): Identification by expression cloning of a novel hematopoietic growth factor related to murine IL-3." Cell 47:3 (1986).
Ihle and Weinstein, Adv. Immuno. 39:1 (1986).
Dorssers et al., "Characterization of a human multilineage-colony-stimulating factor cDNA clone identified by a conserved noncoding sequence in mouse interleukin-3." Gene 55:115 (1987).
Kaushansky et al., "Role of carbohydrate in the function of human granulocyte-macrophage colony-stimulating factor," Biochemistry 26:4861 (1987).
Berman and Lasky, "Engineering glycoproteins for use as pharmaceuticals." Trends in Biotechnology 3:51 (1985).
Miyajima et al., "Expression of murine and human GM-CSFs in S. cerevisiae: Mutagenesis of the potential glycosylation sites." EMBO J. 5:1193–1197 (1986).
Lopez et al., "Recombinant Human Interleukin-3 Stimulation of Hematopoiesis in Humans: Loss of Responsiveness with Differentiation in the Neutrophilic Myeloid Series." Blood 72:1797 (1988).
Otsuka et al., "Isolation and Characterization of an Expressible cDNA Encoding Human IL-3." J. Immunol. 140:2288 (1988).
Gillis et al., "Production of Recombinant Human Colony Stimulating Factors in Yeast" Behring Inst. Mitt. 83:1 (1988).
Urdal et al., "Molecular Characterization of Colony-Stimulating Factors and Their Receptors: Human Interleukin-3." Ann. N.Y. Acad. Sci 554:167 (1989).
Cosman et al., "Human Interleukin-3 and Granulocyte-Macrophage Colony Stimulating Factor: Site-Specific Mutagenesis and Expression in Yeast." Develop. biol. Standard. 69:9 (1988).
Zoller et al., "Oligonucleotide-directed mutagenesis using M 13-derived vectors: an efficient and general procedure for the production of point mutations in any fragment of DNA." Nucl. Acids Res. 10: 6487–6500 (1982).
Wells et al., "Cassette mutagenesis: an efficient method for generation of multiple mutations at defined sites." Gene 34:315–323 (1985).
Kurzrock et al. "Phase I Study of Recombinant Human Interleukin-3 in Patients with Bone Marrow Failure." Blood 74(7):154a (1989).
Ganser et al. "Effects of Recombinant Human Interleukin-3 in Patients with Myelodysplastic Syndromes." Blood 76(3):455–462 (1990).
Ganser et al. "Effects of Recombinant Human Interleukin-3 in Patients with Normal Hematopoieses and in Patients with Bone Marrow Failure." Blood 76(4):666–676 (1990).
Ganser et al. "Effects of Recombinant Human Interleukin-3 in Aplastic Anemia." Blood 76(7):1287–1292 (1990).
Park et al. "Interleukin-3, GM-CSF, and G-CSF Receptor Expression on Cell Lines and Primary Leukemia Cells: Receptor Heterogeneity and Relationship to Growth Factor Responsiveness." Blood 74(1):56–65 (1989).

Primary Examiner—Garnette D. Draper
Attorney, Agent, or Firm—Scott G. Hallquist; Patricia Anne Perkins; Christopher L. Wight

[57] ABSTRACT

The present invention provides a pharmaceutical compositions comprising as active ingredients certain truncated purified human IL-3(Pro$^8$Asp$^{15}$Asp$^{70}$) analog proteins expressed by transformed yeast of the species Saccharomyces cerevisiae, which when administered to a primate do not result in detectable urticaria.

4 Claims, No Drawings

NONGLYCOSYLATED HUMAN INTERLEUKIN-3 ANALOG PROTEINS

BACKGROUND OF THE INVENTION

The present invention relates generally to lymphokines, and particularly to pharmaceutical compositions comprising selected truncated nonglycosylated analog interleukin-3 (IL-3) proteins which exhibit beneficial clinical and toxicological properties when compared to huIL-3 proteins produced in *E. coli*.

The differentiation and proliferation of hematopoietic cells is regulated by secreted glycoproteins collectively known as colony stimulating factors (CSFs). In murine and human systems, these proteins include granulocyte-macrophage colony stimulating factor (GM-CSF), which promotes granulocyte and macrophage production from normal bone marrow, and which also appears to regulate the activity of mature, differentiated granulocytes and macrophages. Other CSFs include macrophage CSF (M-CSF or CSF-1), which induces the selective proliferation of macrophages, and granulocyte CSF (G-CSF) which induces development of granulocyte progenitors from bone marrow precursors. An additional CSF, isolated first in murine systems and more recently from human cell sources, has been designated IL-3 or multi-CSF.

Murine IL-3 was originally identified by Ihle et al., *J. Immunol.* 126:2184 (1981) as a factor which induced expression of a T cell associated enzyme, 20α-hydroxysteriod dehydrogenase. The factor was purified to homogeneity and shown to regulate the growth and differentiation of numerous subclasses of early hematopoietic and lymphoid progenitor cells. cDNA clones corresponding to murine IL-3 were first isolated by Fung et al., *Nature* 307:233 (1984) and Yokota et al., *Proc. Natl. Acad. Sci.* USA 81:1070 (1984). Gibbon and human genomic DNA homologues of the murine IL-3 sequence were disclosed by Yang et al., *Cell* 47:3 (1986). The human sequence reported by Yang et al. included a serine residue at position 8 of the mature protein sequence. Following this finding, three groups reported isolation of Pro$^8$ huIL-3 cDNAs, including Dorssers et al., *Gene* 55:115 (1987); Otsuka et al., *J. Immunol.* 140:2288 (1988); and Gillis et al., *Behring Inst. Mitt.* 83:1 (1988).

A survey of individuals to determine the frequency of the Pro$^8$ allele was reported by Gillis et al., supra. In this work, the polymerase chain reaction was employed to amplify the DNA sequences flanking the position 8 locus. Radiolabeled oligonucleotide probes complementary to the Ser$^8$ and Pro$^8$ forms were then used to probe amplified DNA isolated from thirteen genetically unrelated individuals. Amplified DNA was immobilized on nitrocellulose and analyzed by hybridization under conditions of increasing stringency. The results indicated that of the 13 persons examined, each was positive for DNA encoding the Pro$^8$ version of huIL-3. Three were also positive for Ser$^8$ huIL-3 at this locus (i.e., were heterozygotes), indicating a moderate level of polymorphism of the human IL-3 gene in this test population.

Preclinical and clinical studies of human IL-3 proteins produced by various manufacturers has revealed surprising differences in clinical utility and toxicity. Development of non-toxic, tolerable forms of human IL-3 for therapy is important because recombinant human IL-3 appears to be the first cytokine capable of stimulating granulopoiesis, erythropoiesis and, most important, thrombopoiesis in vivo.

Severe rIL-3 toxicity was reported by Valent et al. at the *First International Symposium: Cytokines in Hemopoiesis, Oncology and AIDS*, held in Hanover, Federal Republic of Germany, Jun. 14-17, 1989. A composition of huIL-3 (Ser$^8$) produced in *E. coli* was evaluated in vivo by administration to rhesus monkeys (n=10) thrice daily at different dosages (0, 11, 33, and 100 μg/kg/day, s.c.) for 14 days followed by consecutive GM-CSF application (days 14-28, 5 μg/kg thrice daily). All monkeys responded to rhuIL-3 by a 2-3 fold white blood cell (WBC) increase by day 14 due to an increase in eosinophils and basophils. Intracellular histamine (IH) in WBC was found to rise continuously after IL-3 treatment until day 8-10. This excess of IH was accompanied by a rise in plasma histamine values and an urticaria-like exanthem revealing infiltration of mast cells and lymphocytes into the dermis observed in skin biopsy specimens. The clinical side effects of this rhuIL-3 composition were attributed to basophil/mast cell activation and histamine-producing effects of this cytokine.

In contrast, the protein compositions of the present invention did not exhibit any detectable urticaria or stimulate infiltration of mast cells or lymphocytes into the dermis when administered to cynomolgus monkeys or human patients. The results of these toxicological and clinical studies are reported in the Examples.

SUMMARY OF THE INVENTION

The present invention provides a pharmaceutical composition comprising as active ingredient one or more purified recombinant human IL-3 (Pro$^8$ Asp$^{15}$ Asp$^{70}$) analog proteins expressed by a transformed yeast host of the species *Saccharomyces cerevisiae*, said proteins selected from the group consisting of:

(a) Met$^3$ rhuIL-3 (Pro$^8$ Asp$^{15}$ Asp$^{70}$);
(b) Thr$^4$ rhuIL-3 (Pro$^8$ Asp$^{15}$ Asp$^{70}$); and
(c) Thr$^6$ rhuIL-3 (Pro$^8$ Asp$^{15}$ Asp$^{70}$).

Such compositions, when infused into a primate, do not result in observable urticaria or infiltration of mast cells and lymphocytes into the dermis.

DETAILED DESCRIPTION OF THE INVENTION

The huIL-3 protein compositions of the present invention comprise selected truncated huIL-3 analog proteins which vary slightly at the N-terminus from the native protein. The utility of such truncated proteins was observed when mixtures of proteins resulted from expression of cDNAs encoding mature huIL-3 proteins in *S. cerevisiae*, presumably as a result of proteolysis by the yeast expression host. As noted above, these mixtures can comprise one or more human IL-3 (Pro$^8$ Asp$^{15}$ Asp$^{70}$) analog proteins having N termini at Met$^3$, Thr$^4$ or Thr$^6$ of the following amino acid sequence (the alternative N-termini are underlined):

Ala Pro <u>Met</u> Thr <u>Gln</u> Thr Thr Pro Leu Lys Thr Ser Trp Val Asp

Cys Ser Asn Met Ile Asp glu Ile Ile Thr His Leu Lys Gln Pro

Pro Leu Pro Leu Leu Asp Phe Asn Asn Leu Asn Gly Glu Asp Gln

Asp Ile Leu Met Glu Asn Asn Leu Arg Arg Pro Asn Leu Glu Ala

Phe Asn Arg Ala Val Lys Ser Leu Gln Asp Ala Ser Ala Ile Glu

Ser Ile Leu Lys Asn Leu Leu Pro Cys Leu Pro Leu Ala Thr Ala

-continued

Ala Pro Thr Arg His Pro Ile His Ile Lys Asp Gly Asp Trp Asn

Glu Phe Arg Arg Lys Leu Thr Phe Tyr Leu Lys Thr Leu Glu Asn

Ala Gln Ala Gln Gln Thr Thr Leu Ser Leu Ala Ile Phe.

The term rhuIL-3 (Pro$^8$ Asp$^{15}$ Asp$^{70}$) means a recombinant human interleukin-3 polypeptide having a proline residue at position 8 and ospartic acid residues at positions 15 and 70, wherein residue 1 refers to the first amino acid of the mature native or wild-type human interleukin-3. The amino acid sequence of such a polypeptide is set forth above. The various N-terminal species are indicated by designating the N-terminal residue before the term "rhuIL-3", e.g., Met$^3$ rhuIL-3 (Pro$^8$ Asp$^{15}$ Asp$^{70}$). Deletions of amino acids are also conventionally referred to using a "$\Delta$" symbol; for example, a truncated, non-glycosylated IL-3 analog having an N-terminus at Met$^3$ would be referred to as $\Delta^{1-2}$ Met$^3$ rhuIL-3(Pro$^8$ Asp$^{15}$ Asp$^{70}$). The analog proteins of the present invention have an aspartic acid (Asp) residue substituted for each asparagine in the N-glycosylation sites present in the native human IL-3 sequence to preclude N-glycosylation by the yeast host at these sites.

A DNA segment encoding human IL-3 was isolated from a cDNA library as described in the Experimental section below. Site-specific oligonucleotide mutagenesis was then performed to provide a cDNA encoding human IL-3 (Pro$^8$ Asp$^{15}$ Asp$^{70}$) The resulting altered cDNA was employed to construct a yeast expression vector, which was used to transform an appropriate yeast expression strain, which was grown in culture under conditions promoting derepression of the yeast promoter. The resulting protein was then purified by a combination of reversed-phase high-performance liquid chromatography (RP-HPLC) and ion-exchange chromatography to provide a purified product. Assay of this product using a human bone marrow proliferation assay and human IL-3 receptor binding assay confirmed expression of an analog product suitable for human pharmaceutical use. N-terminal sequencing of the product revealed a mixture of analog proteins which varied slightly from lot to lot. To obtain a composition consisting essentially of a single species, Met$^3$ huIL-3 (Pro$^8$ Asp$^{15}$ Asp$^{70}$), a second expression vector was constructed wherein the sequence encoding the yeast secretion leader was directly fused in-frame to a construct lacking the codons specifying the first two amino acids of the mature protein.

Preferably, the compositions of the invention consist essentially of Met$^3$ huIL-3 (Pro$^8$ Asp$^{15}$ Asp$^{70}$). However, if an expression vector encoding the full-length mature protein is employed, a mixture will be obtained comprising Ala$^1$ huIL-3 (Pro$^8$ Asp$^{15}$ Asp$^{70}$) in admixture with one or more proteins selected from the foregoing group, typically comprising:

(a) from about 30 to about 40 percent Ala$^1$ huIL-3 (Pro$^8$ Asp$^{15}$ Asp$^{70}$);

(b) from about 10 to about 30 percent Met$^3$ huIL-3 (Pro$^8$ Asp$^{15}$ Asp$^{70}$); and (c) a remainder fraction substantially consisting of a mixture of Thr$^4$ and Thr$^6$ huIL-3(Pro$^8$ Asp$^{15}$ Asp$^{70}$).

Preferably, the compositions of the invention exhibit a specific biological activity in the human bone marrow assay of from about 1.8 to about $7.0 \times 10^7$ U/mg, and preferably 4.0 to about $7.0 \times 10^7$ U/mg, and a binding affinity for human monocyte IL-3 receptors, expressed as an inhibition constant, of from about 2.0 to about $8.0 \times 10^{10}$ M$^{-1}$, preferably from about 4.0 to about $8.0 \times 10^{10}$ M$^{-1}$. It is understood that minor fractions (less than 1 mole %) of rhuIL-3 proteins having other N-termini may also be present in the mixtures of the present invention.

1. ASSAYS FOR HUIL-3 BIOLOGICAL ACTIVITY

Assays used to measure huIL-3 biological activity are described below.

A. Human Bone Marrow Proliferation Assay

Freshly isolated human bone marrow cells are preincubated for 2 hours at 37° C., 5% $CO_2$, in tissue culture flasks containing $2 \times 10^6$ cells per ml prewarmed, pregassed serum-free RPMI1640 medium (Gibco, Chagrin Falls, OH, USA) containing 50 units/ml penicillin, 50 μg/ml streptomycin, and 300 μg/ml fresh L-glutamine (hereinafter "assay medium"). After preincubation, nonadherent cells are removed by pipetting the media gently over the surface of the flask. Nonadherent cells are collected by centrifugation at 1000 rpm for 10 minutes at 4° C., resuspended in a small volume of assay medium containing 10% fetal bovine serum (FBS), and counted using Trypan blue for viability and Turks stain for recovery of white cells. Cells are kept at about 4° C. in assay medium containing 10% FBS until added to assay plates.

50 μl assay medium are added to each well of a 96 well flat bottom tissue culture plate. 50 μl of sample diluted in assay medium are added to the first well of each row, and serial dilutions are made across each row in the usual manner. $1.25 \times 10^4$ bone marrow cells, in a volume of 100 μl, are then added to each well. Plates are incubated for 4 days at 37° C., 5% $CO_2$, in a plastic box containing sterile distilled $H_2O$ to prevent desiccation. On day 4, 25 μl of assay medium containing 5% FBS and 80 μCi/ml [$^3$H]-thymidine (80 Ci/mmol) are added to each well and the plate incubated 5 hr at 37° C., 5% $CO_2$, in a plastic box. After incubation, cells are harvested onto glass fiber filters, washed, and tested for incorporated radioactivity using a scintillation counter. Units of huIL-3 activity are calculated by reference to the quantity of huIL-3 which induces 50% of maximal thymidine incorporation. For example, if a 100 μl sample generates one-half maximal thymidine incorporation at a dilution of 1:20, one unit is defined as the activity contained in 1/20 of 100 μl, or 5 μl. The sample would therefore contain 1000 divided by 5, or 200 units per milliliter (U/ml) of huIL-3 activity.

B. Human IL-3 Receptor Binding Assay

In a 96-well round bottom microtiter plate, ten 2-fold dilutions of each sample are prepared in RPMI 1640 medium beginning at 0.075 μg/ml (50 μl each). For each assay plate, triplicate 50 μl aliquots of rhuIL-3 standards (1.5 μg/ml) and negative controls (binding medium) are set up. For purposes of this assay, "binding medium" means RPMI 1640 with 2.5% (w/v) bovine serum albumin (BSA), 0.2% (w/v) sodium azide, and 20 mM HEPES, pH 7.2. 50 μl of $^{125}$I rhu IL-3 stock ($1 \times 10^{-9}$M in binding medium, specific activity $4-8 \times 10^{15}$ cpm/mmole), prepared as described in PCT application U.S. Ser. No. 89/02599, are then added to each well, followed by 50 μl of human monocytes (harvested from culture by centrifugation, washed twice with RPMI 1640, and resuspended to $4 \times 10^7$ cells/ml in binding medium). Each plate is then incubated for 1 hour at 37° C. on a rotary shaker with vigorous mixing. After incubation, cells and bound $^{125}$I rhuIL-3 are separated from unbound $^{125}$I rhuIL-3 by a phthalate oil centrifugation technique, conducted as follows. First, duplicate 65 μl aliquots are removed from each incubation mixture, and each aliquot is layered onto 200 μl of a cold phthalate oil mixture [1.5 parts dibutyl phthalate, 1 part bis(-2-ethylhexyl)-phthalate (Eastman Kodak Co., Rochester, NY)] in 400 μl polyethylene centrifuge tubes and centrifuged for 1 minute in a microcentrifuge at 8° C. The cells plus bound $^{125}$I rhuIL-3 sediment through the phthalate oil mixture while the less dense binding medium containing unbound $^{125}$I rhuIL-3 is left on its surface. $^{125}$I rhuIL-3 bound to cells is measured by cutting the tubes in half and counting top and tip portions for $^{125}$I. The results of the IL-3 receptor binding assay are expressed as inhibition (%) calculated according to Equation 1 below:

$$I(\%) = \frac{100 \times (Max - Test)}{(Max - Min)} \qquad \text{Equation 1}$$

when Max is the level of binding of $^{125}$I IL-3 in the presence of medium alone, Min is the level of binding in the presence of 1.5 μg/ml unlabeled and Test is the binding level in the presence of test sample dilutions. Results are analyzed by non-linear least squares fitting Equation 2 below:

$$M(\%) = \frac{M \cdot K_I \cdot I}{1 + K \cdot C + K_I \cdot I} \qquad \text{Equation 2}$$

to the data expressed in the form given in 1 where M (%) is the maximal level of inhibition, K ($M^{-1}$) is the binding constant of $^{125}$I rhu IL-3, C (M) is the concentration of $^{125}$I rhu IL-3, I (M) is the concentration of the test sample and $K_I$ ($M^{-1}$) is the inhibition (binding) constant of the test sample. The values of $K_I$ for test samples are scaled to that of an rhuIL-3 standard by dividing [$K_I/K_S$] when $K_S$ is the inhibition constant of the standard, to yield a relative binding activity.

2. PROTEIN EXPRESSION IN RECOMBINANT YEAST SYSTEMS

Recombinant *Saccharomyces cerevisiae* host cells are used for expression of the recombinant proteins of this invention. Preferred expression vectors can be derived from pBC102.K22 (ATCC 67255) which contains DNA sequences from pBR322 for selection and replication in *E. coli* ($Ap^r$ gene and origin of replication) and yeast DNA sequences including a glucose-repressible alcohol dehydrogenase 2 (ADH2) promoter. The ADH2 promoter has been described by Russell et al., *J. Biol. Chem.* 258:2674 (1982) and Beier et al., *Nature* 300:724 (1982). Plasmid pBC102.K22 also includes a Trp1 gene as a selectable marker and the yeast 2μ origin of replication. Adjacent to the promoter is the yeast α-factor leader sequence enabling secretion of heterologous proteins from a yeast host. The α-factor leader sequence is modified to contain, near its 3′ end, an Asp718 (Kpnl and Asp718 are isoschizomers) restriction site to facilitate fusion of this sequence to foreign genes. A sequence coding for the Glu-Ala-Glu-Ala amino acids was omitted to allow efficient processing of secreted protein, as described by Brake et al., *Proc. Natl. Acad. Sci. USA* 81:4642 (1984).

Alternative expression vectors are yeast vectors which comprise an α-factor promoter, for example pYαHuGM (ATCC 53157), which bears the wild-type human GM-CSF gene. Others are known to those skilled in the art. The construction of pYαHuGM is described in published European Patent Application No. 183,350 (8530682.7), the disclosure of which is incorporated by reference herein.

The choice of appropriate yeast strains for transformation will be determined by the nature of the selectable markers and other features of the vector. Appropriate *S. cerevisiae* strains for transformation by expression vectors derived from pBC102.K22 or pYαHuGM include strains X2181-1B, available from the Yeast Genetic Stock Center, Berkely, CA, USA (see below), having the genotype α trp1 gal1 ade1 his2; J17 (ATCC 52683; α his2 ade1 trp1 met14 ura3); and IL166-5B (ATCC 46183; α his1 trp1). A particularly preferred expression strain for use with pBC102-K22, XV2181, is a diploid formed by mating two haploid strains, X2181-1B, available from the Yeast Genetic Stock Center, Department of Biophysics and Medical Physics, University of California, Berkeley, CA 94702, USA; and XV617-1-3B, available from the Department of Genetics, University of Washington, Seattle, WA 98105, USA, or Immunex Corporation, 51 University Street, Seattle, WA 98101, USA. A suitable transformation protocol is that described by Hinnen, et al., *Proc. Natl. Acad. Sci.* USA 75:1929 (1978), selecting for Trp+ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 or α-factor promoters are grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and frozen or held at 4° C. prior to further purification.

3. PURIFICATION OF IL-3

Recombinant huIL-3 resulting from fermentation of yeast strains can be purified by single or sequential reversed-phase HPLC steps on a preparative HPLC column, by methods analogous to those described by Urdal et al., *J. Chromatog.* 296:171 (1984) and Grabstein et al., *J. Exp. Med.* 163:1405 (1986). A preferred purification protocol is described in Example 2, below.

EXPERIMENTAL DISCUSSION

Example A

Isolation of cDNA Encoding huIL-3

Peripheral blood lymphocytes were isolated from buffy coats prepared from whole blood (Portland Red Cross, Portland, Oreg., USA) by Ficoll hypaque density centrifugation. T cells were isolated by rosetting with 2-aminoethylthiouronium bromide-treated sheep red blood cells. Cells were cultured in 175 cm² flasks at $5 \times 10^6$ cells/ml for 18 hour in 100 ml RPMI, 10% fetal calf serum, 50 μM β-mercaptoethanol, 1% phytohemagglutinin (PHA) and 10 ng/ml phorbol 12-myristate 13-acetate (PMA). RNA was extracted by the guanidinium CsCl method and poly A+ RNA prepared by oligo-dT cellulose chromatography (Maniatis et al., *Molecular Cloning: A Laboratory Manual*, Cold Spring Harbor, 1982). cDNA was prepared from poly A+ RNA essentially as described by Gubler and Hoffman, *Gene* 25:263-269 (1983). The cDNA was rendered double-stranded using DNA polymerase I, blunt-ended with T4 DNA polymerase, methylated with EcoRI methylase to protect EcoRI cleavage sites within the cDNA, and ligated to EcoRI linkers. These constructs were digested with EcoRI to remove all but one copy of the linkers at each end of the cDNA, ligated to EcoRI-cut and dephosphorylated arms of bacteriophage λgt10 (Huynh et al., *DNA Cloning: A Practical Approach*, Glover, ed., IRL Press, pp. 49-78), and packaged into λphage extracts (Stratagene, San Diego, CA, USA) according to the manufacturer's instructions. 500,000 recombinants were plated on *E. coli* strain C600hfl-and screened by standard plaque hybridization techniques using the following probes.

Two oligonucleotides were synthesized, with sequences complementary to selected 5' and 3' sequences of the huIL-3 gene. The 5' probe, complementary to a sequence encoding part of the huIL-3 leader, had the sequence 5'-GAGTTGGAGCAGGAGCA-GGAC-3'. The 3' probe, corresponding to a region encoding amino acids 123-130 of the mature protein, had the sequence 5'-GATCGCGAGGC TCAAAGTCGT-3'.

The method of synthesis was a standard automated triester method substantially similar to that disclosed by Sood et al., *Nucl. Acids Res.* 4:2557 (1977) and Hirose et al., *Tet. Lett.* 28:2449 (1978). Following synthesis, oligonucleotides were deblocked and purified by preparative gel electrophoresis. For use as screening probes, the oligonucleotides were terminally radiolabeled with $^{32}$P-ATP and T4 polynucleotide kinase using techniques similar to those disclosed by Maniatis et al. The *E. coli* strain used for library screening was C600hfl-(Huynh et al., 1985, supra).

Thirteen positive plaques were purified and reprobed separately with the two hybridization probes. Eleven clones hybridized to both oligonucleotides. The cDNA inserts from several positive recombinant phage were subcloned into an EcoRI-cut derivative (pGEMBL18) of the standard cloning vector pBR322 containing a polylinker having a unique EcoRI site, a BamH1 site and numerous other unique restriction sites. An exemplary vector of this type, pEMBL, is described by Dente et al., *Nucl. Acids Res.* 11:1645 (1983), in which the promoters for SP6 and T7 polymerases flank the multiple cloning sites. The nucleotide sequences of selected clones were determined by the chain termination method. Specifically, partial EcoR1 digestion of IGT10:IL-3 clones 2, 3, 4 and 5 yielded fragments ranging from 850 bp to 1,000 bp in size which were separately subcloned into the EcoR1 site of pGEMBL18. The inserts of the pGEMBL:rhuIL-3 subclones were sequenced using a universal primer that binds adjacent to the multiple cloning site of pGEMBL18, and synthetic oligonucleotide primers derived from the huIL-3 sequence.

EXAMPLE 1

Modification of N-Glycosylation Sites Encoded by huIL-3 cDNA and Assembly of Expression Vector for rhuIL-3 (Pro$^8$ Asp$^{15}$ Asp$^{70}$)

The two asparagine-linked glycosylation sites present in the natural protein (Asn$^{15}$ and Asn$^{70}$) were altered by changing the codons at these positions to ones that encode aspartic acid. This prevents N-linked glycosylation (often hyperglycosylation) of the secreted protein by the yeast cells, and a more homogeneous product is obtained. These changes were made as described below upon subcloning the huIL-3 cDNA into the yeast expression vector PIXY120.

The yeast expression vector pIXY120 is substantially identical to pBC102.K22, described in EPA 243,153, except that the following synthetic oligonucleotide containing multiple cloning sites was inserted from the Asp718 site (amino acid 79) near the 3' end of the α-factor signal peptide to the SpeI site contained in the 2μsequences.

In addition, a 514-bp DNA fragment derived from the single-stranded bacteriophage f1 containing the origin of replication and intergenic region was inserted at the Nru1 site in the pBR322 DNA sequences. The presence of the f1 origin of replication enables generation of single-stranded copies of the vector when transformed into appropriate (male) strains of *E. coli* and superinfected with bacteriophage f1. This capability facilitates DNA sequencing of the vector and allows the possibility of in vitro mutagenesis.

The yeast expression vector pIXY120 was digested with the restriction enzymes Asp718, which cleaves near the 3' end of the α-factor leader peptide (nucleotide 237), and BamH1, which cleaves in the polylinker. The large vector fragment was purified and ligated to the following DNA fragments: (1) a huIL-3 cDNA fragment derived from plasmid GEMBL18:huIL-3 from the Cla 1 site (nucleotide 58 of mature huIL-3) to the BamH1 site (3' to the huIL-3 cDNA in a polylinker); and (2) the following synthetic oligonucleotide linker A:

```
GTA CCT TTG GAT AAA AGA GAC TAC AAG GAC GAC GAT GAC AAG GCT CCC ATG ACC CAG
    GA AAC CTA TTT TCT CTG ATG TTC CTG CTG CTA CTG TTC CGA GGG TAC TGG GTC

ACG ACG CCC TTG AAG ACC AGC TGG GTT GAT TGC TCT AAC ATG AT
TGC TGC GGG AAC TTC TGG TCG ACC CAA CTA ACG AGA TTG TAC TAG C
```

Oligonucleotide A regenerates the sequence encoding the C-terminus of the α-factor leader peptide and fusing it in-frame to the octapeptide DYKDDDDK, which is, in turn, fused to the N-terminus of mature rhuIL-3. This fusion to the rhuIL-3 protein allows detection with antibody specific for the octapeptide and was used initially for monitoring the expression and purification of rhuIL-3. This oligonucleotide also encodes an amino acid change at position 15 (Asn[15] to Asp[15]) to alter this N-linked glycosylation site. The underlined nucleotides in oligonucleotide A represent changes from the wild type cDNA sequence. Only the A to G and C to T changes at nucleotides 43 to 45, respectively (counting from the codon corresponding to the N-terminal alanine of the mature huIL-3 molecule), result in an amino acid change (Asp[15]). The other base changes introduce convenient restriction sites (AhaII and PvuII) without altering the amino acid sequence. The resulting plasmid was designated pIXY139 and contains a rhuIL-3 cDNA with one remaining N-linked glycosylation consensus sequence (Asn[70]).

Plasmid pIXY139 was used to perform oligonucleotide-directed mutagenesis to remove the second N-linked glycosylation consensus sequence by changing Asn[70] to Asp[70]. The in vitro mutagenesis was conducted by a method similar to that described by Walder and Walder, *Gene* 42:133 (1986). The yeast vector, pIXY139, contains the origin of replication for the single-stranded bacteriophage f1 and is capable of generating single-stranded DNA when present in a suitable (male) strain of *E. coli* and superinfected with helper phage.

Single-stranded DNA was generated by transforming *E. coli* strain JM107 and superinfecting with helper phage IR1. Single-stranded DNA was isolated and annealed to the following mutagenic oligonucleotide B, GTC AAG AGT TTA CAG GAC GCA TCA GCA AAT G, which provides a codon switch substituting Asp for Asn at position 70 of mature huIL-3. Annealing and yeast transformation conditions were done as described by Walder and Walder, supra. Yeast transformants were selected by growth on medium lacking tryptophan, pooled, and DNA extracted as described by Holm et al., *Gene* 42:169 (1986). This DNA, containing a mixture of wild type and mutant plasmid DNA, was used to transform *E. coli* RR1 to ampicillin resistance. The resulting colonies were screened by hybridization to radiolabeled oligonucleotide B using standard techniques. Plasmids comprising DNA encoding huIL-3 Asp[70] were identified by the hybridization to radiolabeled oligonucleotide B under stringent conditions and verified by nucleotide sequencing.

The resulting yeast expression plasmid was designated pIXY138, and contained the huIL-3 gene encoding the Asp[15] Asp[70] amino acid changes and the octapeptide DYKDDDDK at the N-terminus. The final yeast expression plasmid is identical to pIXY138 except that it lacks the nucleotide sequences coding for the octapeptide, thus generating mature rhuIL-3 as the product.

The final yeast expression plasmid was constructed as described below. The yeast expression vector pIXY120 was cleaved with the restriction enzymes Asp718 and BamH1 as described above. The large vector fragment was ligated together with (1) a huIL-3 cDNA fragment derived from plasmid pIXY138 that extended from the AhaII site (which cleaves a nucleotide 19 of mature huIL-3) to the BamH1 site 3' to the cDNA, and (2) the following synthetic oligonucleotide C:

```
    GTA CCT TTG GAT AAA AGA GCT CCC ATG ACC CAG ACG A
        GA AAC CTA TTT TCT CGT GGG TAC TGG GTC TGC TGC
        Pro Leu Asp Lys Arg Ala Pro Met Thr Gln Thr Thr
```

Oligonucleotide C regenerates the 3' end of the α-factor leader peptide from the Asp718 site (the amino acids Pro-Leu-Asp-Lys-Arg) and the N-terminal seven amino acids of huIL-3 to the AhaII site. The resulting plasmid was designated pIXY151. This vector, when present in yeast, allows glucose-regulated expression and secretion of rhuIL-3 (Pro[8] Asp[15] Asp[70]). In order to provide relatively homogeneous compositions consisting largely of Met[3] rhuIL-3 (Pro[8] Asp[15] Asp[70]), a similar expression vector, designated pIXY290, was constructed using a substitute oligonucleotide identical to Oligonucleotide C but lacking the codons specifying the Ala and Pro residues present in the native human IL-3 protein. When transfected into a suitable host which is then grown under appropriate conditions, this vector is capable of directing expression of rhuIL-3 preparations which are substantially completely composed of the Met[3] rhuIL-3 (Pro[8] Asp[15] Asp[70]) product (see Example 3, below).

EXAMPLE 2

Expression and Purification of rhuIL-3 (Pro[8] Asp[15] Asp[70]) Mixture

The host strain, XV2181, a diploid S. cerevisiae strain, was formed by mating XV617-1-3B [α, his6, leu2-1, trp1-1, ura 3, ste5], obtained from the University of Washington, Department of Genetics Yeast Strain Bank, Seattle, WA, USA, and X2181-1B [α, trp1-1, gal1, ade1, his2], obtained from the Yeast Genetic Stock Center, University of California, Berkeley, CA, USA. The host strain is transformed with the expression plasmid by the method of Sherman et al., *Laboratory Course Manual for Methods in Yeast Genetics*, Cold Spring Harbor Laboratory, 1986.

Yeast containing the expression plasmid pIXY151 (see Example 1, above) are maintained on YNB-trp agar plates stored at 4° C. A preculture is started by inoculating several isolated recombinant yeast colonies into one liter of YNB-trp medium (6.7 g/L Yeast Nitrogen Base, 5 g/L casamino acids, 40 mg/L adenine, 160 mg/L uracil, and 200 mg/L tyrosine), and is grown overnight in two 2-liter flasks at 30° C. with vigorous shaking. By morning the culture is saturated, in stationary phase, at an $OD_{600}$ of 2 to 7. The fermenters (three machines of 10 liter working volume), previously cleaned and sterilized, are filled to 80% of their working capacity with SD-2 medium (4.0 g/L ammonium sulfate, 3.2 g/L monobasic potassium phosphate, 3.0 g/L yeast extract, 1.0 g/L citric acid, 0.1 g/L sodium chloride, 5 ml/L 2% calcium chloride, 2.5 ml/L vitamin 101 solution, 0.5 ml/L trace elements solution, 0.5 ml/L 20% magnesium sulfate, 2.0 ml/L glucose) and maintained at 30° C. with 500–600 rpm agitation and 10–≠1pm aeration. The inoculum is added. After two hours of growth a nutrient feed of 50% glucose is begun at a rate such that 50 g/L is added over a period of 10–12 hours. The nutrient feed is then shifted to 50% ethanol added at 30–40 ml/hr until harvest.

Total elapsed time of fermentation is approximately 20 hours, after which optical density (600 nm) ranges from 30 to 45. The fermenters are then cooled to 20° C., pH of the yeast beer is adjusted to 8.0 by the addition of 5M NaOH, and the resulting material filtered through a Millipore Pellicon filter system equipped with a 0.45 μm filter cassette, and collected in a sterile 10 L carboy.

The rhuIL-3 contained in the yeast broth is applied to a 5 cm×30 cm column packed with 15-20 μm C-4 reversed-phase silica (Vydac, Separations Group, Hesperia, CA, USA) by pumping the filtered yeast broth directly onto the column. The column is equilibrated in 0.1% trifluoroacetic acid in water (Solvent A) prior to application of the yeast broth and is flushed with this solvent following the completion of the application of the broth to the column until the optical absorbance of the effluent approaches base line values. At this time a gradient of 0.1% trifluoroacetic acid in acetonitrile (Solvent B) is established from 0% B to 100% B at a rate of change of 2% B per minute and at a flow rate of 100 ml/minute. A pause of five minutes when the gradient reaches 30% B is programmed into the gradient controller. Twenty minutes after the initiation of the gradient, one minute fractions are collected. Aliquots of the fractions are analyzed for protein content by a fluorescamine assay using bovine serum albumin (BSA) as a standard. RhuIL-3 was found to elute in fractions 8, 9 and 10. Fractions containing rhuIL-3 from the first step are stored at 4° C. in polyethylene bottles until approximately 1 gram total protein is obtained. To the pool is added 2 volumes of 0.1% trifluoroacetic acid in water. This solution is then pumped onto a second 5 cm×30 cm column packed with 15-20μ C-18 silica (Vydac, Separations Group, Hesperia, CA, USA) that is equilibrated in Solvent A (0.1% TFA in water). Following application of the material, the column is flushed with Solvent A and then a gradient identical to that described above is established at a rate of change of 1% Solvent B per minute and at a flow rate of 100 ml/min. Fractions are collected every 0.4 minutes 24 minutes into the gradient. Aliquots of the fractions are analyzed for protein content by the fluorescamine assay using BSA as a standard.

Peak fractions from the C-18 column are pooled and 1/10 volume of 0.5M β-alanine pH 3.6 is added. A sample is taken and then the pool is applied to a 10 ml S-Sepharose Column (1 cm×10 cm, Pharmacia) at 5 ml/minute. After sample application, the column is washed with 50 ml of 10 mM Tris, pH 7.4 and the IL-3 is eluted with a linear gradient from 10 mM Tris, pH 7.4 to 200 mM Tris, pH 7.4 (200 ml total gradient volume). Peak fractions of rhuIL-3 are then pooled and dialyzed against 100 mM Tris, pH 7.4, overnight at 4° C., then sterile filtered.

The biological activities (units/mg) and binding affinities of three production lots of rhuIL-3 prepared substantially as described above were determined. Binding affinity was assessed by determination of inhibition constants ($K_i$) using purified proteins. The results are set forth in Table I, below. In Table I, all values are expressed as the averages of samples run in triplicate in two separate assays.

The rhuIL-3 of these three lots (AZZ-0001-0003) was also subjected to protein sequencing by Edman degradation and the integrated value (pmole) of each PTH amino acid residue was compared to the known protein sequence. A line for each concurrent sequence was obtained by linear regression analysis and used to estimate the prevalence (%) of each sequence in the preparation. The results are set forth below.

TABLE 1

| N-Terminal Composition, Specific Activity and Binding Affinity of rhuIL-3 Production Lots | | | | | |
|---|---|---|---|---|---|
| | Species: Mole % | | | | Specific Activity | Binding Affinity |
| Lot | $Ala^1$ | $Met^3$ | $Thr^4$ | $Thr^6$ | ($\times 10^7$ U/mg) | ($\times 10^{10} M^{-1}$) |
| AZZ-0001 | 34 | 23 | 31 | 12 | 4.5 | 5.58 |
| AZZ-0002 | 35 | 15 | 11 | 39 | 5.6 | 7.14 |
| AZZ-0003 | 37 | 18 | 14 | 31 | 5.0 | 5.95 |

EXAMPLE 3

Fermentation and Purification of $Met^3$ rhuIL-3 ($Pro^8$ $Asp^{15}$ $Asp^{70}$)

The expression vector pIXY290 (see Example 1, above) was transfected into the S. cerevisiae production strain XV2181 substantially as described for pIXY151 in Example 2.

An inoculum was prepared by inoculating 0.5 mL of a frozen glycerol stock of the production strain into a 6 L flask containing (a) 500 ml of a yeast growth medium containing per liter sterile $H_2O$: 20.0 g $(NH_4)_2SO_4$; 5.0 g $KH_2PO_4$; 1.0 g $MgSO_4 \cdot 7H_2O$;) 0.1 g $CaCl_2 \cdot 2 H_2O$; 10.0 g casein digest; 20.0 g glucose and 20.0 g galactose; (b) 0.5 ml of a trace salts mix containing, per liter sterile $H_2O$: 5.0 g boric acid, 2.0 g copper sulfate, 10.0 g ferric chloride; 10.0 g manganese sulfate; 0.5 g sodium molybdate; 1.0 g zinc sulfate; 0.5 g cobalt chloride; and 100 ml 6N HCl; and (c) 0.5 ml of a vitamin solution containing, per liter sterile $H_2O$: 1.0 ml of a 0.2% solution of biotin; 1,.0 g calcium pantothenate; 25.0 g myo-inositol; 5.0 g niacin; 0.4 g pyridoxine-HCl; 0.1 g folic acid; and 0.5 g choline chloride. This inoculum culture was incubated at 30° C. in a rotary flask shaker at 250 rpm for approximately 24 hours.

A 10 liter fermenter was prepared for fermentation by filling with 7.5 L deionized $H_2O$ containing 50 g monobasic potassium phosphate, 200 g ammonium sulfate, 10 g $MgSO_4 \cdot 7H_2O$, 1.0 g $CaCl_2 \cdot 2H_2O$, and 2 ml of a anti-foaming surfactant. The fermenter was then sterilized by heating to 121° C. for 30 minutes with stirring. After sterilization, the fermenter was supplemented with 35 ml 1% (w/v) thiamine-HCl, 500 ml 10% casein hyrolysate, 100 ml 50% glucose, and 25 ml each of the vitamin and trace salts solutions described above. Fermenter pH was controlled to pH 5.5 by addition of 30% $NH_4OH$, and dissolved $O_2$ was spanned at 100 percent at 29° C. The contents of the inoculum were then added to the fermenter and a feed started at about 2.0 ml per minute of a feed solution consisting of (a) 3600 ml 50% glucose; (b) 625 ml of a yeast feed salts solution consisting of (per liter H2O): 250 g ammonium sulfate, 125 g monobasic potassium phosphate, and 25 g $MgSO_4 \cdot 7H_2O$; (c) 900 ml 50 EtOH; (d) 60 ml 1% thiamine-HCl; (e) 450 ml 20% yeast extract; (f) 450 ml 20% peptone; (g) 900 ml 20% casein hydrolysate; and (h) 25 ml each of the vitamin and trace salts solutions described above. The feed rate was maintained at this level for about 20 hours, then adjusted to 3.25 ml per minute for about 20 hours, whereupon the culture supernatant was harvested substantially as described in Example 2, above.

The rhuIL-3 contained in the yeast broth was first reduced by adjusting to 1% beta mercaptoethanol at pH 7.4, then incubating for 1 hour at ambient temperature. The resulting mixture was applied to a 5 cm×30 cm column packed with 15-20 μm C-4 reversed-phase silica (Vydac, Separations Group, Hesperia, CA, USA) by pumping the filtered yeast broth directly onto the column. The column was equilibrated in 0.1% trifluoroacetic acid in water (Solvent A) prior to application of the yeast broth and was flushed with this solvent following the completion of the application of the broth to the column until the optical absorbance of the effluent approaches base line values. At this time a gradient of 0.1% trifluoroacetic acid in acetonitrile (Solvent B) was established from 0% B to 100% B at a rate of change of 2% B per minute and at a flow rate of 100 ml/minute.

Peak fractions from the C-4 column were pooled and adjusted to 50 mM sodium acetate, pH 4.7. This solution was then applied directly to a column containing Mono S ion exchange resin equilibrated in 50 mM sodium acetate pH 4.7, and rhuIL-3 was eluted with a linear gradient of 1M NaCl over 20 column volumes. The resulting rhuIL-3 was substantially 100% $Met^3$ rhuIL-3 ($Pro^8 Asp^{15} Asp^{70}$), and comparable in biological activity to the rhuIL-3 production lots described in Example 2, above.

EXAMPLE 4

Intravenous Administration of rhuIL-3 ($Pro^8 Asp^{15} Asp^{70}$) Compositions to Cynomolgus Monkeys Three groups of three male and three female cynomolgus monkeys (*Macaca fascicularis*) each received material from one of the rhuIL-3 lots prepared as described in Example 2 via intravenous administration once daily for 30 consecutive days at dose levels of 1 μg/kg (Group 2, low-dose), 10 μg/kg (Group 3, mid-dose), and 100 μg/kg (Group 4, high-dose). A fourth group of three males and three females received 0.9% sodium chloride (saline) and seved as the control group (Group 1, control). One animal per sex per group was retained for a 17-day recovery period. Criteria evaluated for compound effect included survival, clinical signs, physical, electrocadiographic and ophthalmoscopic examinations, changes in body temperature, body weight, clinical pathology, organ weight data, and gross and microscopic pathology.

All animals survived until their scheduled sacrifice. Treatment-related clinical signs included anorexia. No urticaria was noted. No treatment-related effects were noted in body weights, physical examination, electrocadiographic evaluation or ophthalmoscopic examinations. Clinical pathology parameters evaluated included hematology and myeloid/erythroid (M/E) ratios evaluated from femoral smears. Serum chemistry and urinalysis was also performed. Notable serum chemistry parameters for the mid- and high-dose animals were unremarkable when compared to concurrent control values or respective pretreatment values. Urinalysis values obtained following treatment were unremarkable.

Intravenous injection of analog rhuIl-3 dramatically increased the leukocyte counts in mid- and high-dose males and females. Mean lymphocyte count values were also increased in cell-treated males and high-dose females. Increases in segmented neutrophils, eosinophils, and basophils in mid- and high-dose animals in general paralleled the increased leukocyte and lymphocyte counts. An increase was also observed for the mean platelet counts for the high-dose males and compound-treated females during the treatment interval. The most notable dose-related increases occurred progressively during first and second week with a general decline toward pretreatment levels during post-recovery phase.

Gross pathology noted certain abnormalities of spleen, thymus, and adrenal glands in individual animals receiving the highest dosages. However, no two animals showed the same effect and in one case, the abnormality was diagnosed as a preexisting condition. An increased mean absolute relative thymus weight was noted for low- and mid-dose males at terminal sacrifice and one low-dose and one mid-dose female at post-recovery sacrifice. Microscopic findings noted in the animals sacrificed at termination were few in number and were primarily minimal to slight in severity. All histopathology findings were considered incidental in nature and unrelated to compound administration.

EXAMPLE 5

Clinical Evaluation of IL-3 Compositions

The rhuIL-3 of one or more of the production lots prepared as described in Example 2 was administered for 15 days as a daily subcutaneous injection to patients with advanced progressive neoplasms or bone marrow failure. Regular routine hematological and biochemical investigations were done and bone marrow aspirations and biopsies were obtained prior to and after treatment cycles. A total of 14 patients were treated at 60, 125, 250 and 500 μg/m². No patient stopped therapy due to toxicity. In all nine evaluable patients, substantial increases in WBC, absolute segmented granulocyte, eosinophil and monocyte counts, as well as in reticulocyte and platelet counts, were seen. Hematological changes, in particular the increase in platelet counts, occurred primarily during the second week of rhuIL-3 treatment and continued for 1-2 weeks after the end of therapy. The mean increase of platelet counts was 179,500/μl (63,000-448,000). In two patients with prolonged thrombocytopenia of 3000/μl and 22,500/μl, respectively, the platelet counts rose to 104,000/μl and 88,000/μl for an extended period of time after treatment with 60 μg/m². Toxicities included fever in three patients (grade 2), headache in one patient (grade 2) and local erythema at the injection site (grade 1) in one patient. Urticaria or infiltration of mast cells or lymphocytes into the dermis was not observed.

What is claimed is:

1. A substantially homogeneous and purified recombinant human IL-3 analog protein consisting essentially of $\Delta^{1-2}Met^3$ huIL-3 ($Pro^8 Asp^{15} Asp^{70}$).

2. A purified recombinant human IL-3 analog protein according to claim 1, having a specific biological activity in a human bone marrow assay of from about 1.8 to about $7.0 \times 10^7$ U/mg.

3. A method for treating neutropenia, anemia or thrombocytopenia in a patient in need thereof, comprising administering a therapeutically effective amount of a composition according to claim 1.

4. A method for treating neutropenia, anemia, or thrombocytopenia in a patient in need thereof, comprising administering a therapeutically effective amount of a composition according to claim 2.

* * * * *